United States Patent
Goel et al.

(10) Patent No.: US 11,420,993 B2
(45) Date of Patent: Aug. 23, 2022

(54) SEMI-SYNTHETIC MENINGOCOCCAL CONJUGATE VACCINE

(71) Applicant: Biological E Limited, Telangana (IN)

(72) Inventors: Akshay Goel, Hyderabad (IN); Santosh Renukuntla, Hyderabad (IN); Eswara Kowlakuntla, Hyderabad (IN); Mahima Datla, Hyderabad (IN); Narender Dev Mantena, Hyderabad (IN)

(73) Assignee: Biological E Limited

( * ) Notice: Subject to any disclaimer, the term of this patent is extended or adjusted under 35 U.S.C. 154(b) by 34 days.

(21) Appl. No.: 16/437,561

(22) Filed: Jun. 11, 2019

(65) Prior Publication Data

US 2019/0389894 A1 Dec. 26, 2019

Related U.S. Application Data

(62) Division of application No. 15/313,393, filed as application No. PCT/IN2015/000218 on May 22, 2015, now abandoned.

(30) Foreign Application Priority Data

May 24, 2014 (IN) ........................ IN1570/CHE/2014

(51) Int. Cl.
| | | |
|---|---|---|
| *C07H 15/04* | (2006.01) | |
| *A61K 39/095* | (2006.01) | |
| *C07H 1/00* | (2006.01) | |
| *A61K 39/00* | (2006.01) | |

(52) U.S. Cl.
CPC ........... *C07H 15/04* (2013.01); *A61K 39/095* (2013.01); *C07H 1/00* (2013.01); *A61K 2039/6037* (2013.01)

(58) Field of Classification Search
None
See application file for complete search history.

(56) References Cited

FOREIGN PATENT DOCUMENTS

| WO | WO 2003/007985 | 1/2003 |
| WO | WO 2002/058737 | 8/2008 |
| WO | WO 2010/111703 | 9/2010 |
| WO | WO 2011/149778 | 12/2011 |
| WO | WO 2014/097099 | 6/2014 |
| WO | WO 2016/055957 | 4/2016 |

OTHER PUBLICATIONS

Fusco et al, (Clinical and Vaccine Immunology, 14(5):577-584, 2007).*
Broker et al (Human Vaccinesand Immunotherapeutics, 12(7):1808-1824, 2016).*
Chu et al., "Efficient and Stereoselective Synthesis of [alpha](2->9) Oligosialic Acids: From Monomers to Dodecamers," Angew Chem Int Ed 50(40):9391-5 (publication date: Sep. 26, 2011, epublication date: Aug. 29, 2011).
International Search Report and Written Opinion dated Nov. 25, 2015 for International Application No. PCT/IN2015/000218.
Kubler-Kielb et al., "A New Method for Conjugation of Carbohydrates to Proteins Using an Aminooxy-Thiol Heterobifunctional Linker," J. Org. Chem. 70(17):6987-90 (publication date: Aug. 19, 2005, epublication date: Jul. 27, 2005).
Kubler-Kielb et al., "Oligosaccharide conjugates of Bordetella pertussis and bronchiseptica induce bactericidal antibodies, an addition to pertussis vaccine," PNAS 108:4087-92 (publication date: Mar. 8, 2011, epublication date: Feb. 22, 2011).
Kubler-Kielb et al.,"Saccharide/protein conjugate vaccines for Bordetella species: preparation of saccharide, development of new conjugation procedures, and physico-chemical and immunological characterization of the conjugates," Vaccine 26(29-30):3587-93 (publication date: Jul. 4, 2008, epublication date: May 20, 2008).
Liao et al., "Synthesis and immunological study of [alpha]-2,9-oligosialic acid conjugates as anti-group C meningitis vaccines," Chem Commun. 51(47):9647-50 (publication date: Jun. 14, 2015).
Lin et al., "Phosphite-based sialic acid donors in the synthesis of α(2→9) oligosialic acids," Tetrahedron 65(24):4714-4725 (publication date: Jun. 13, 2009, epublication date: Apr. 16, 2009).
Lin, et al.,"5-N,4-O-carbonyl-7,8,9-tri-O-chloroacetyl-protected sialyl donor for the stereoselective synthesis of alpha-(2-->9)-tetrasialic acid," J. Org. Chem. 75(15):4921-4928 (publication date: Aug. 6, 2010).

* cited by examiner

*Primary Examiner* — Patricia Duffy
(74) *Attorney, Agent, or Firm* — Perkins Coie LLP

(57) ABSTRACT

The present invention relates to novel semi-synthetic meningococcal conjugate vaccine comprising novel synthetic oligosaccharide conjugated to a carrier protein. The present invention also relates to novel synthetic meningococcal oligosaccharide and a process for its preparation.

7 Claims, 7 Drawing Sheets

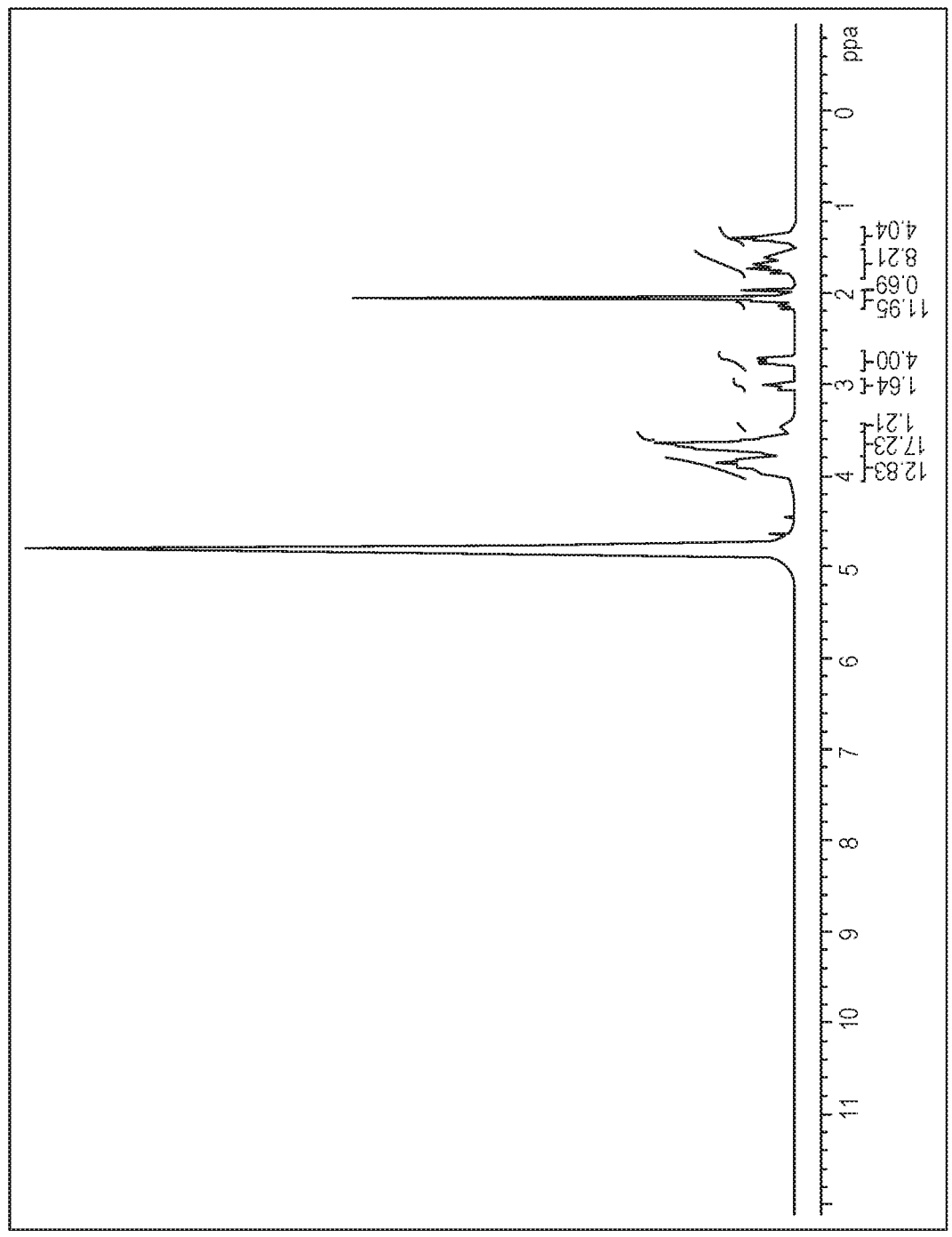
Fig. 1: ¹H NMR of the Semi-synthetic Meningococcal C oligomer with Linker.

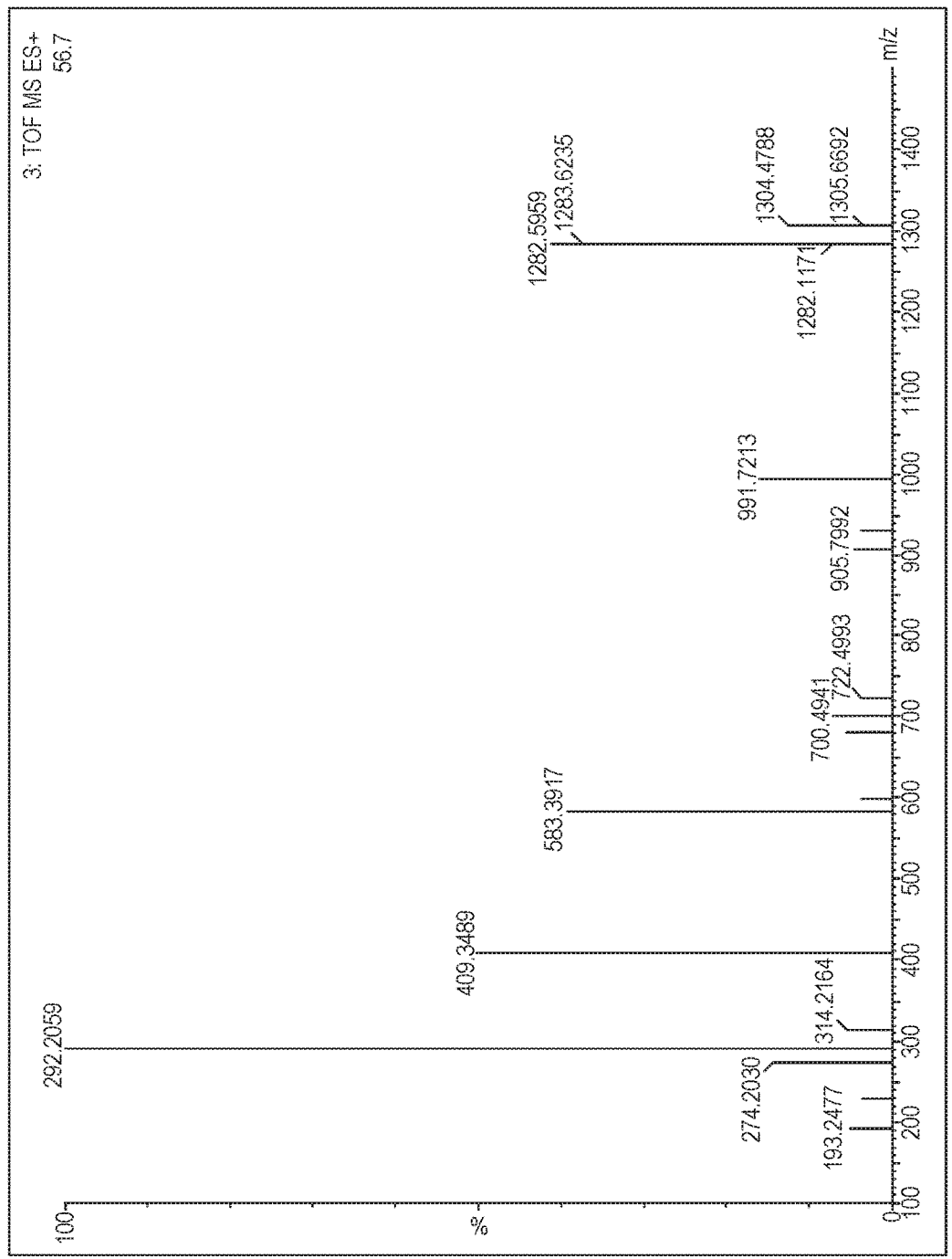
Fig. 2: High Resolution Mass Spectroscopy (HRMS) data for the synthetic Meningococcal C oligomer.

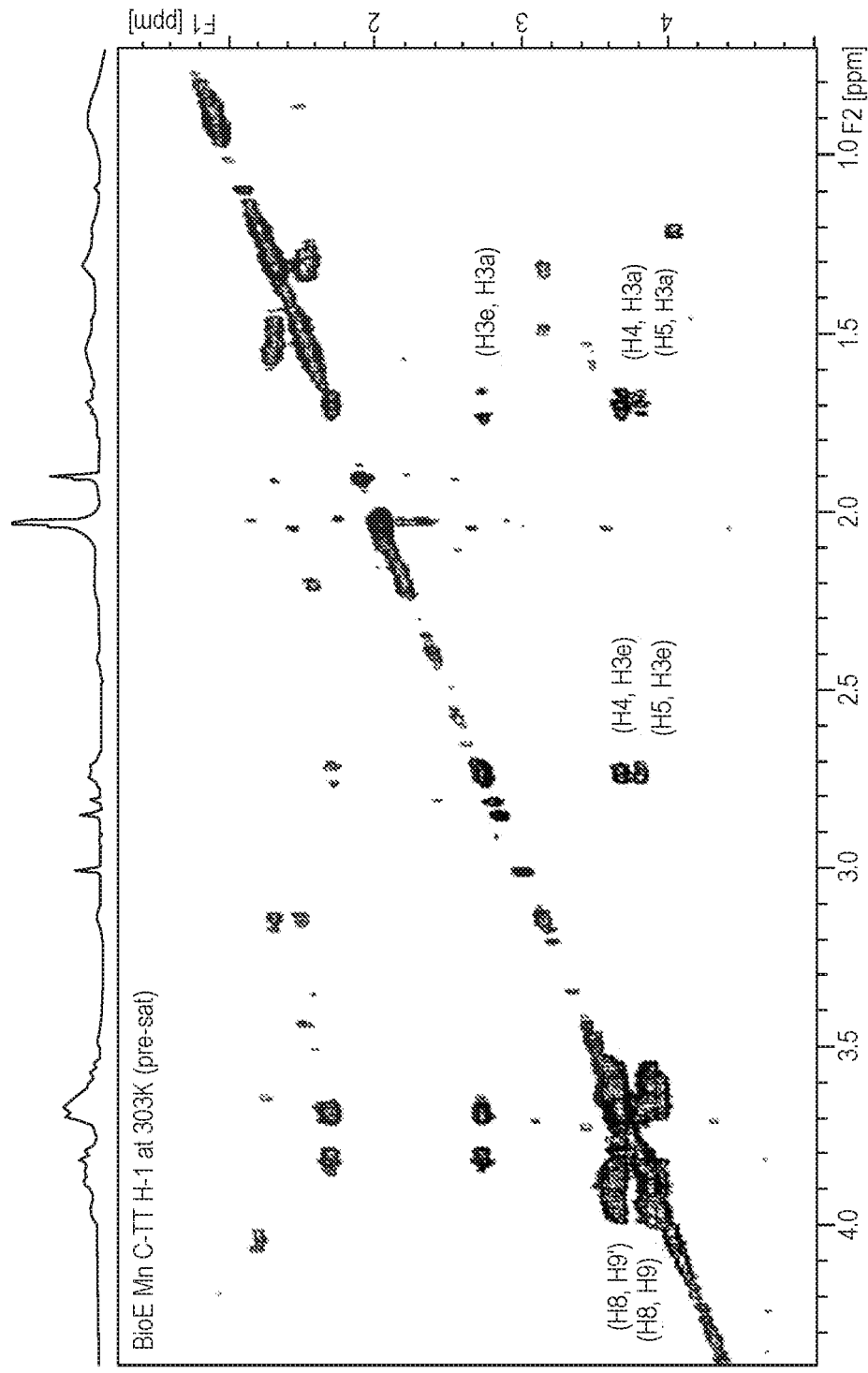
Fig. 3: TOCSY (120 ms) of semisynthetic Meningococcal C bulk conjugate.

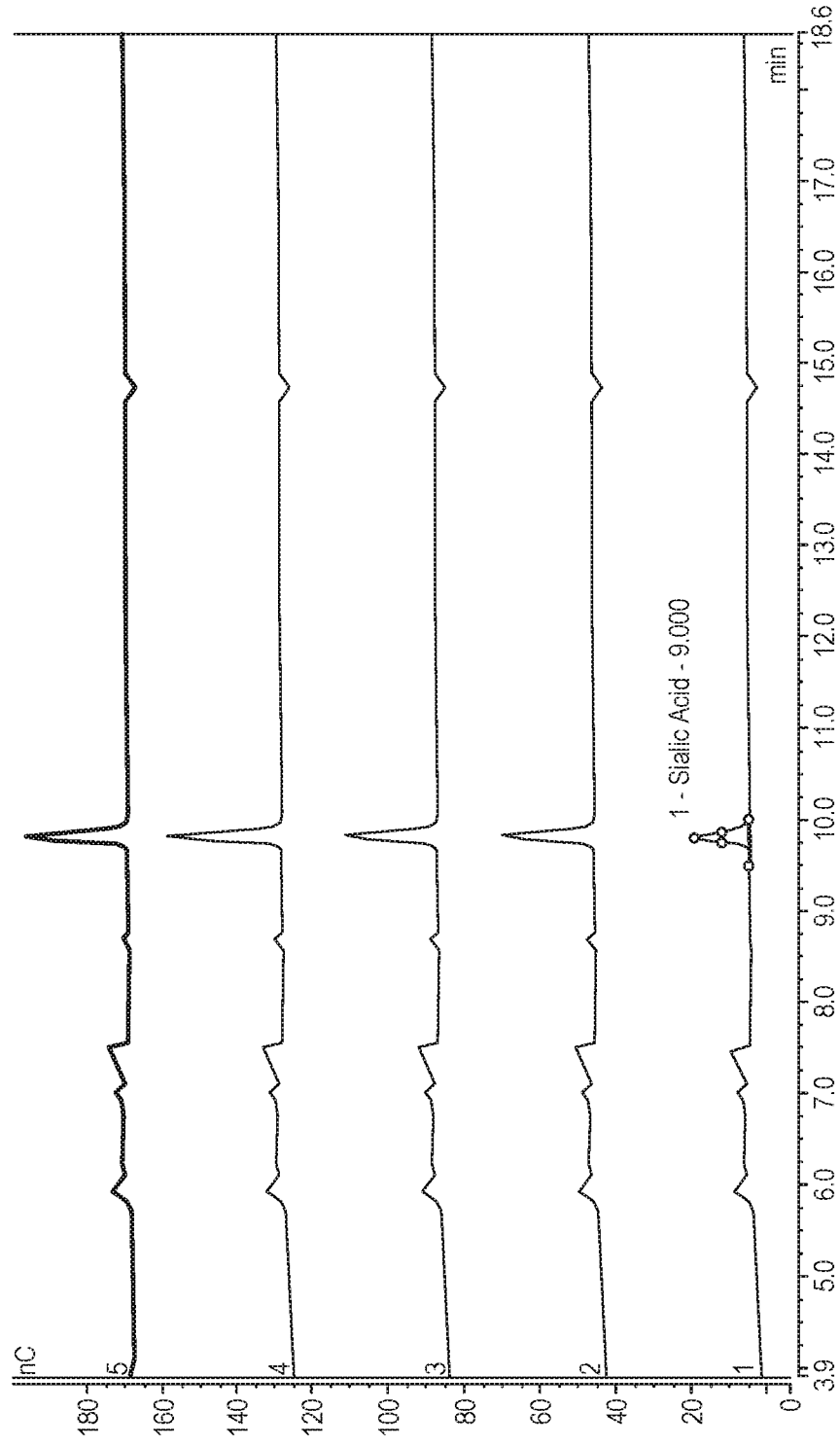
Fig. 4: Quantification of Sialic acid in semi synthetic Meningococcal-C Conjugate Using Sialic acid as reference standard by HPAEC-PAD Method.

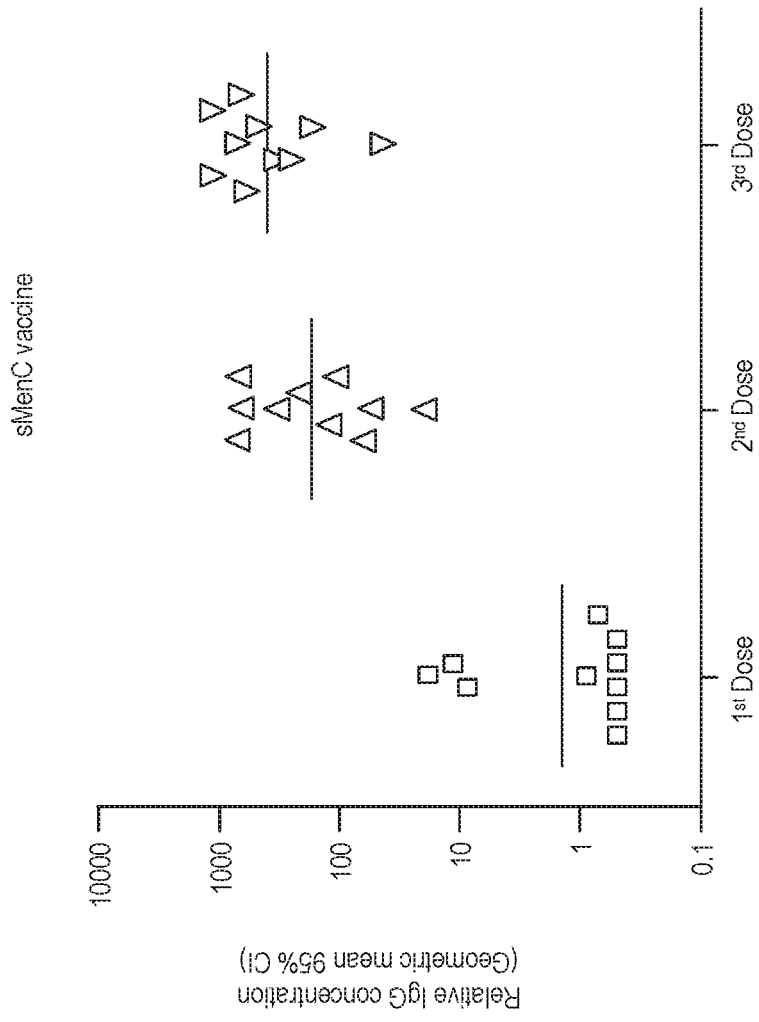
Fig. 5: Individual Mice IgG concentration for anti-meningococcal C polysaccharide IgG levels measured by serotype specific ELISA.

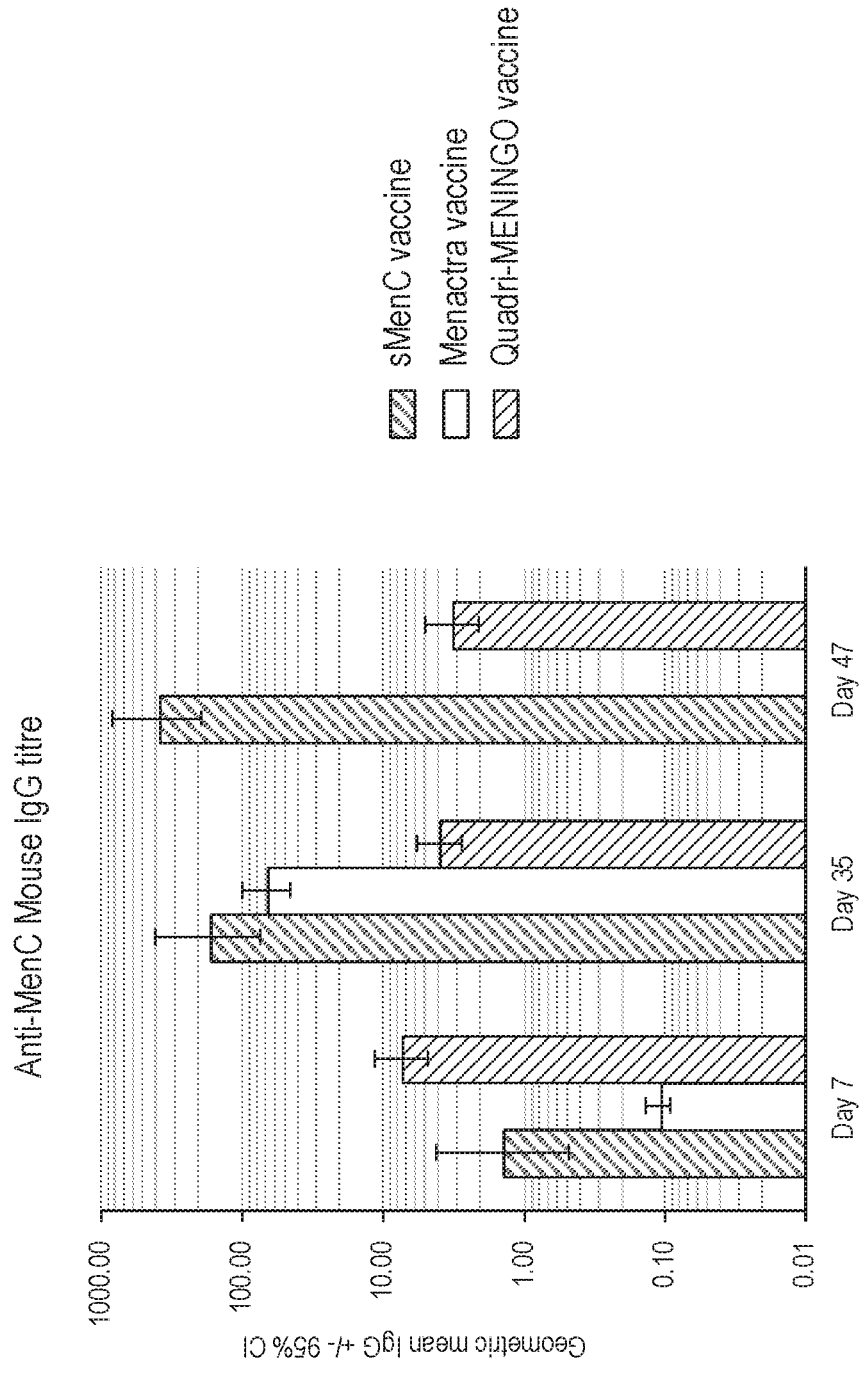
Fig. 6: Geometric mean anti-MenC IgG concentrations for groups of mice following immunisation with test vaccine formulations.

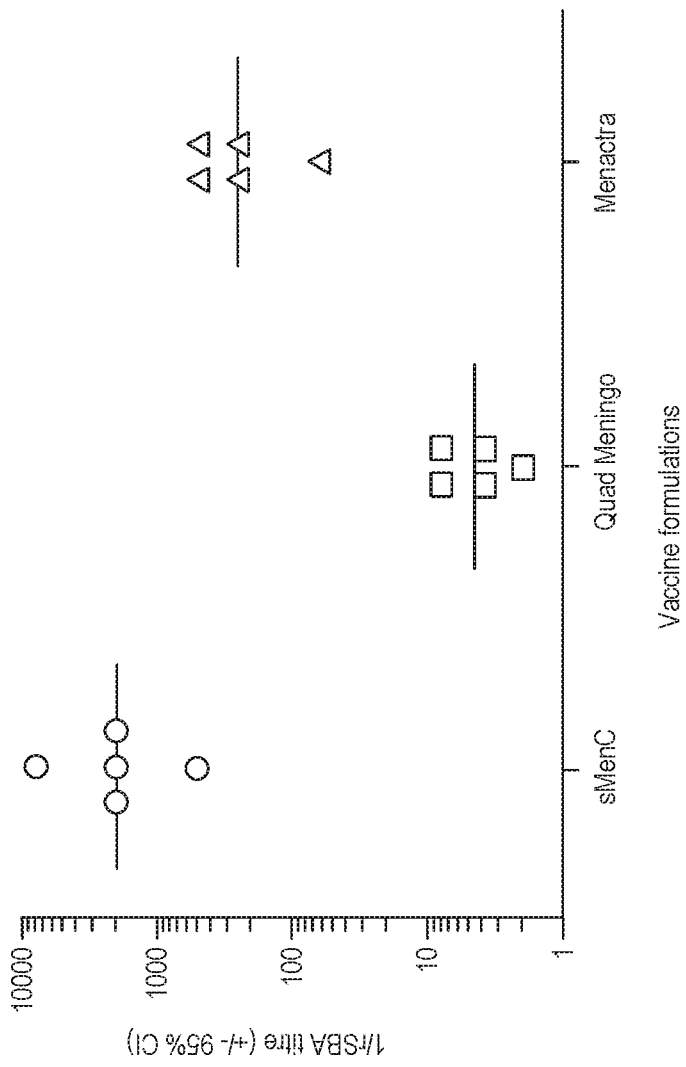
Fig. 7: Relative rSBA titre for sera obtained following immunisation with sMenC after last Dose in each case of vaccine formulations, geometric mean is displayed as bar.

SEMI-SYNTHETIC MENINGOCOCCAL CONJUGATE VACCINE

PRIORITY CLAIM

This application is a division of U.S. patent application Ser. No. 15/313,393 filed on Nov. 22, 2016, which is a 371 U.S. National Stage Application of International Patent Application No. PCT/IN2015/000218 filed on May 22, 2015, which claims priority to Indian Patent Application Serial No. 1570/CHE/2014 filed on May 24, 2014, the entire contents of which are incorporated herein by reference and relied upon.

FIELD OF THE INVENTION

The present invention relates to novel semi-synthetic meningococcal conjugate vaccine comprising novel synthetic oligosaccharide conjugated to a carrier protein. The present invention also relates to novel synthetic meningococcal oligosaccharide and a process for its preparation.

BACKGROUND OF THE INVENTION

*Neisseria meningitidis* is a leading cause of bacterial meningitis and sepsis throughout the world. Meningococcal bacteria incorporate polysaccharides into their surface structure. Thus a large majority of bacteria are covered with capsule or glycocalyx polysaccharide which induces an immunological response in humans. The outer membrane of gram-negative *Neisseria meningitidis* (NM) bacterium consists, inter alia, of lipopolysaccharide (LPS). Such polysaccharides (PS) are formed on the basis of repeating units in which, the constituents and the bonds are defined and which are each characteristics of the NM serogroups. Hence, these repeating units contain the epitopes or the antigenicity determining structures.

Conjugated immunogenic composition comprises of a target antigen (polysaccharide) component chemically conjugated to a carrier protein. These vaccines are known to be highly immunogenic in all age groups including infants. A conjugate comprising an oligosaccharide covalently bound to a carrier protein is also referred to as glyco-conjugate.

The immunogenicity of the capsular polysaccharides can be improved by covalently coupling them to a carrier protein. When covalently linked to a carrier protein, the resulting PS component in a conjugate vaccine becomes a T cell-dependent (TD) antigen, inducing long-term immunity with immune memory even in infants and young children.

WO 02/058737 disclosed immunological compositions for treatment of meningococcal polysaccharide-protein conjugates caused by pathogenic *Neisseria meningitidis*, which comprises two or more protein-polysaccharide conjugates, wherein each of the conjugates comprises a capsular polysaccharide from *N. meningitidis* conjugated to a carrier protein.

WO 03/007985 disclosed a process for purifying a bacterial capsular polysaccharide, comprising the steps of (a) precipitation of the polysaccharide, followed by (b) solubilisation of the precipitated polysaccharide using an alcohol.

Lin, Chang-Ching; et al. (Tetrahedron (2009), 65(24), 4714-4725) disclosed the synthesis of α-(2→9) tetrasialic acid using phosphite donor and iterative sialylations to elongate the sugar chain from the non-reducing end to the reducing end.

Scheme 5

Compound 36

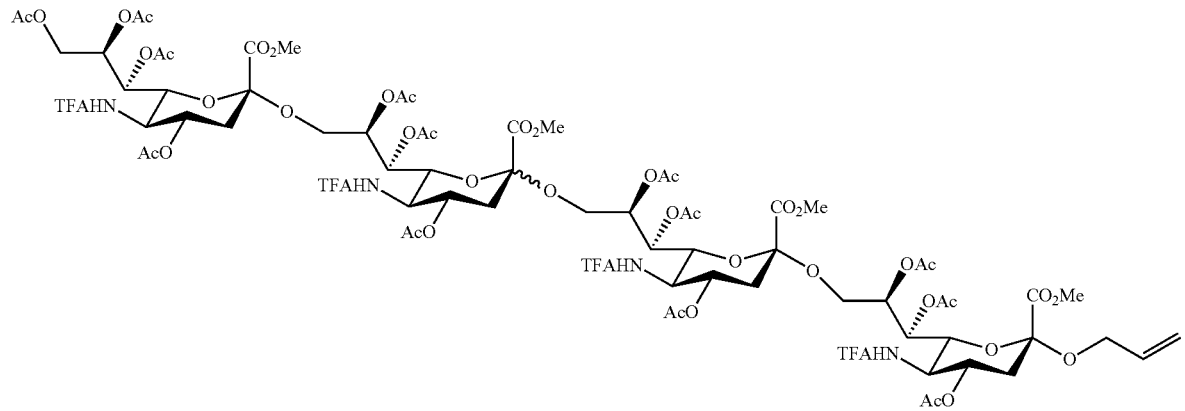

Chang-Ching Lin, et al. (*J. Org. Chem.*, 2010, 75 (15), 4921-4928) disclosed an efficient α-selective method for synthesis of α-(2-+9) tetrasialic acid using 5-N,4-O-carbonyl-protected thioglycoside sialyl donors.

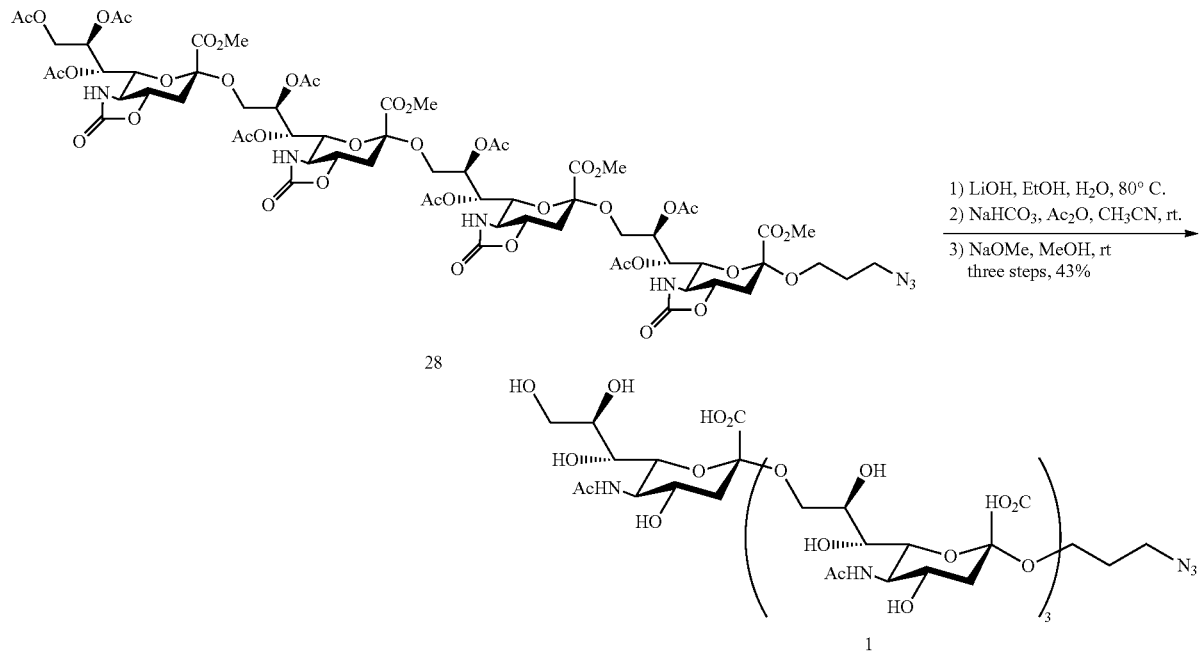

Chu, Kuo-Ching; et al. (Angewandte Chemie, International Edition (2011), 50(40), 9391-9395) disclosed the synthesis of α(2→9)oligosialic acids: from monomers to dodecamers, which are considered to be the current vaccines against meningococcal C diseases. The synthetic route of tetrasialoside and hexasialoside can be used to synthesize the proposed Men C pentamer using 5-N,4-O-carbonyl-protected glycosyl phosphate sialyl donors.

some purification steps to remove impurities such as protein, endotoxins, nucleic acids, need for reduction in size of purified oligosaccharide, need for attachment of a linker to the purified oligosaccharide and low conjugation yields. Hence, a major disadvantage of these conventional biological processes is requirement of repeated purifications, which results in low yields.

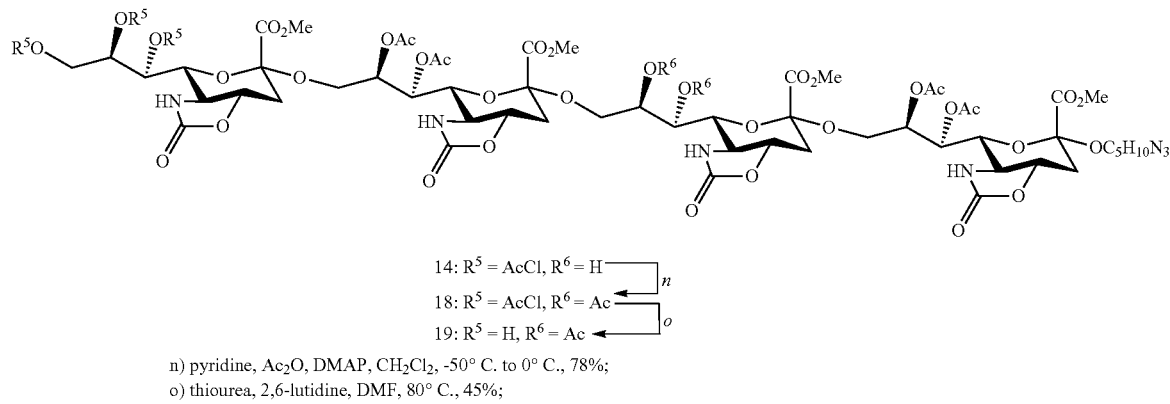

Several meningococcal C conjugate vaccines available in the market as monovalent (e.g. Neisvac-C®, Menjugate®) as well as multivalent products (e.g. Menactra®, Mencevax, Nimenrix, Menveo®). The polysaccharide component in all these vaccines is derived from the fermentation and purification of the actual pathogenic bacteria. The saccharide moiety in glycoconjugate vaccines is usually a functiona- WO 2014/097099 A2 discussed, that prior to activation step the polysaccharide of the invention may be sized to achieve an appropriate molecular weight. This is done either mechanically or simple hydrolyzation.

In order to overcome the disadvantages associated with the preparation of conventional meningococcal oligosaccharides, the inventors of the present invention have found that the conjugation of carrier protein with synthetically made immunogenic oligosaccharide will result in development of a cost effective meningococcal vaccine with non-inferior immunogenicity compared to existing vaccines.

Synthetic polysaccharides have a number of potential advantages over native polysaccharides. There is an ease of production of these polysaccharides without the need for fermentation. Naturally derived carbohydrates are heterogeneous mixtures and may include small amounts of natural impurities and contaminants. In contrast, synthetic carbohydrates can be produced as homogeneous single compounds in a controlled manner, with little or no batch-to-batch variability. Another advantage is that they can be made to include functional groups for derivatization or modification of the carbohydrate moiety that are difficult or impossible to perform with native polysaccharide.

Objective of the Invention

The main objective of the present invention is to provide novel semi-synthetic Men C conjugate vaccine, with non-inferior immunogenicity.

Yet another objective is to provide semi-synthetic Men C conjugate vaccine without using the cumbersome fermentation process and thereby repeated multistep purifications.

Yet another objective of the present invention is to provide impurity free and economically viable Men C conjugate vaccine production.

SUMMARY OF THE INVENTION

Accordingly, the present invention provides a novel synthetic meningococcal C oligosaccharide of formula (I)

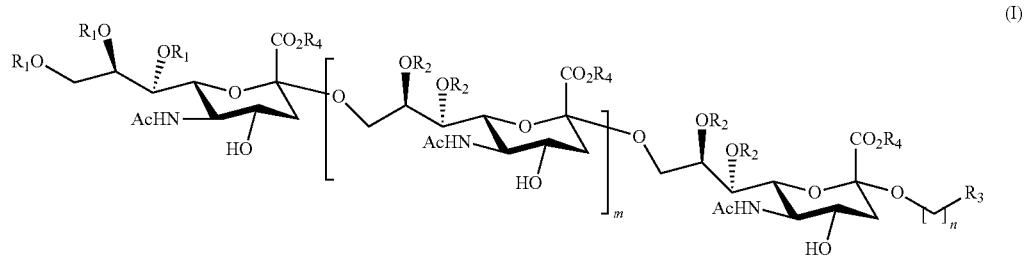

wherein m and n are integers ranging from 1 to 10;
$R_1$ and $R_2$ are same or different and independently represent H, $C_{1-6}$alkyl, acetyl;
$R_3$ represents azide, $NR_5R_6$, wherein $R_5$ and $R_6$ are same or different and independently represent H, $C_{1-6}$ alkyl, aryl;
$R^4$ represents H, $C_{1-6}$ alkyl, alkali metal cation selected from Li, Na, K and Cs; with a proviso that when m=1 to 2, then n is not 1 to 5.

In another embodiment, the present invention provides a novel semi-synthetic meningococcal C conjugate vaccine of the formula (II)

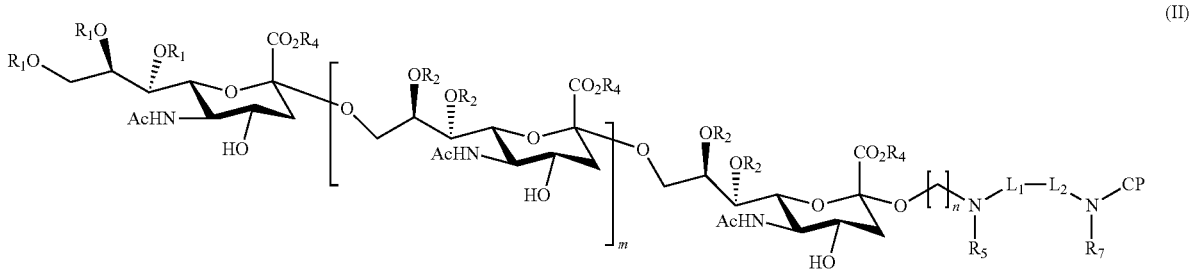

wherein m and n are integers ranging from 1 to 10;
$R_1$ and $R_2$ are same or different and independently represent H, $C_{1-6}$alkyl, acetyl;
$R^4$ represents H, $C_{1-6}$ alkyl, alkali metal cation selected from Li, Na, K and Cs;
$R_5$ represent H, $C_{1-6}$ alkyl, aryl;
CP represents a carrier protein;
$L_1$ is a bond, —O—, —S—, —NR$_8$—, —C(=O)—, —NR$_8$C(=O)—, —NR$_8$C(=O)O—, —C(=O)NR$_8$—, —OC(=O)NR$_8$—, —SC(=O)—, —C(=O)S—, —OC(=O)—, —C(=O)O—, —NR$_8$C(=S)—, —C(=S)NR$_8$—, trans —CR$_9$=CR$_9$—, cis —CR$_9$=CR$_9$—, —C≡C—, —OC(R$_9$)$_2$—, —C(R$_9$)$_2$O—, —NR$_8$C(R$_9$)$_2$—, —C(R$_9$)$_2$NR$_8$— —SC(R$_9$)$_2$—, —C(R$_9$)$_2$S—, —S(=O)$_2$O—, —OS(=O)$_2$—, —S(=O)$_2$NR$_8$—, —NR$_8$S(=O)$_2$—, or an optionally substituted $C_{1-20}$hydrocarbon chain, optionally wherein one or more carbon units of the hydrocarbon chain is replaced with —O—, —S—, —NR$_8$—, —C(=O)—, NR$_8$C(=O)—, —NR$_8$C(=O)O—, —C(=O)NR$_8$—, —OC(=O)NR$_8$— —SC(=O)—, —C(=O)S— —OC(=O)—, —C(=O)O—, —NR$_8$C(=S)—, —C(=S)NR$_8$—, trans-CR$_9$=CR$_9$—, cis-CR$_9$=CR$_9$—, —C≡C— —S(=O)$_2$O—, —OS(=O)$_2$—, —S(=O)$_2$NR$_8$—, or —NR$_8$S(=O)$_2$, wherein R$_8$ is hydrogen, optionally substituted $C_{1-6}$ alkyl, or a nitrogen protecting group, or R$_8$ is joined with the adjacent carbon atom to form an optionally substituted heterocyclic ring, and wherein each occurrence of R$_9$ is independently selected from the group consisting of hydrogen, halogen, optionally substituted $C_{1-10}$ alkyl, optionally substituted alkenyl, optionally substituted alkynyl, optionally substituted carbocyclyl, optionally substituted heterocyclyl, optionally substituted aryl, and optionally substituted heteroaryl, or R$_9$ is joined with the adjacent carbon or nitrogen or oxygen atom to form an optionally substituted carbocyclic or heterocyclic ring, or two R$_9$ groups are joined to form an optionally substituted carbocyclic or optionally substituted heterocyclic ring;

$L_2$ is a moiety derived from a crosslinking reagent capable of crosslinking the carrier and Li;
$R_7$ is independently hydrogen, optionally substituted $C_{1-6}$ alkyl, optionally substituted acyl, or a nitrogen protecting group.
with a proviso that when m is 1 to 2, then n is not 1 to 5.

BRIEF DESCRIPTION OF THE DRAWINGS

FIG. 1: $^1$H NMR of novel synthetic oligosaccharide.
FIG. 2: Molecular weight of synthetic oligosaccharide (HRMS).
FIG. 3: Analytical confirmation (TOCSY) of oligosaccharide in semi-synthetic bulk conjugate.
FIG. 4: Quantification of Sialic acid in semi-synthetic Meningococcal-C Conjugate using sialic acid as reference standard by HPAEC-PAD Method.
FIG. 5: The individual anti-meningococcal polysaccharide IgG antibody levels measured by serotype specific ELISA.
FIG. 6: Geometric mean anti-MenC IgG concentrations for group of mice following immunisation with test and reference vaccine formulations.
FIG. 7: Relative rSBA titre for sera obtained following immunisation with sMenC where the geometric mean is displayed as bar.

DETAILED DESCRIPTION OF THE INVENTION

The capsular polysaccharide of *Neisseria meningitidis* serogroup C is a homopolymer of N-acetyl neuraminic acid bound to −2→9,→9)-D-NeupNAc(7/8OAc)-α-(2→, with O-acetyl group in position C7 and C8 in variable percentage.

The present invention provides a novel synthetic meningococcal C oligosaccharide of formula (I)

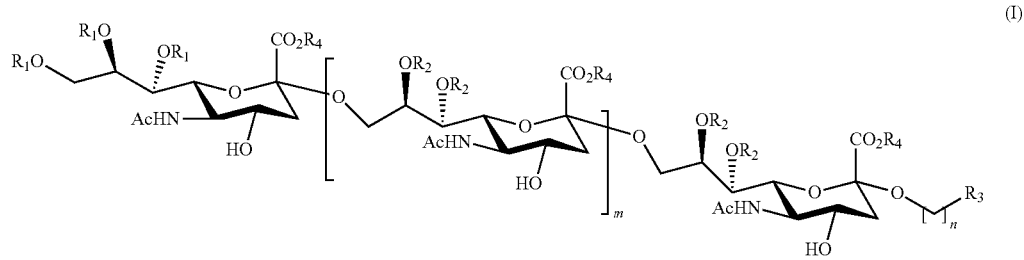

wherein m and n are integers ranging from 1 to 10;
R₁ and R₂ are same or different and independently represent H, $C_{1-6}$alkyl, acetyl;
R₃ represents azide, $NR^5R^6$, wherein $R^5$ and $R^6$ are same or different and independently represent H, $C_{1-6}$ alkyl, aryl;
$R^4$ represents H, $C_{1-6}$ alkyl, alkali metal cation selected from Li, Na, K and Cs; with a proviso that when m=1 to 2 then n is not 1 to 5.

The present invention provides novel semi-synthetic meningococcal C conjugate vaccine of the formula (II)

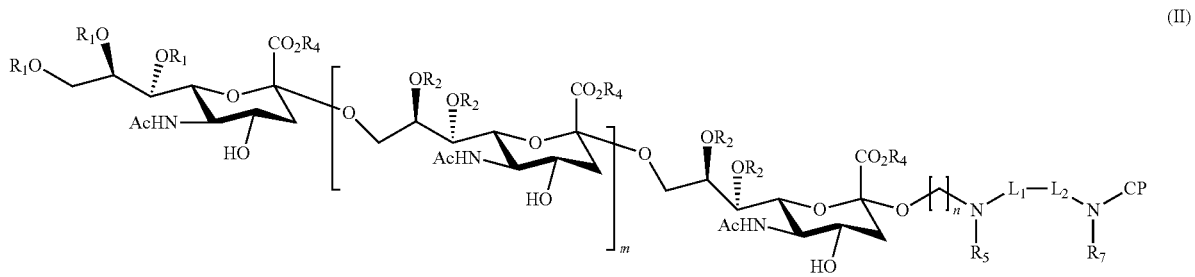

(II)

wherein m and n are integers ranging from 1 to 10;
R₁ and R₂ are same or different and independently represent H, $C_{1-6}$alkyl, acetyl;
$R^4$ represents H, $C_{1-6}$ alkyl, alkali metal cation selected from Li, Na, K and Cs;
R₅ represent H, $C_{1-6}$ alkyl, aryl;
CP represents a carrier protein;
L₁ is a bond, —O—, —S—, —NR₈—, —C(=O)—, —NR₈C(=O)—, —NR₈C(=O)O—, —C(=O)NR₈—, —OC(=O)NR₈—, —SC(=O)—, —C(=O)S—, —OC(=O)—, —C(=O)O—, —NR₈C(=S)—, —C(=S)NR₈—, trans CR₉=CR₉, cis CR₉=CR₉, —C≡C—, —OC(R₉)₂—, —C(R₉)₂O—, —NR₈C(R₉)₂—, —C(R₉)₂NR₈—, —SC(R₉)₂—, —C(R₉)₂S—, —S(=O)₂O—, —OS(=O)₂—, —S(=O)₂NR₈—, —NR₈S(=O)₂—, or an optionally substituted $C_{1-20}$hydrocarbon chain, optionally wherein one or more carbon units of the hydrocarbon chain is replaced with —O—, —S—, —NR₈—, —C(=O)—, NR₈C(=O)—, —NR₈C(=O)O—, —C(=O)NR₈—, —OC(=O)NR₈— —SC(=O)—, —C(=O)S— —OC(=O)—, —C(=O)O—, —NR₈C(=S)—, —C(=S)NR₈—, trans-CR₉=CR₉—, cis-CR₉=CR₉—, —C=C— —S(=O)₂O—, —OS(=O)₂—, —S(=O)₂NR₈—, or —NR₈S(=O)₂, wherein R₈ is hydrogen, optionally substituted $C_{1-6}$ alkyl, or a nitrogen protecting group, or R₈ is joined with the adjacent carbon atom to form an optionally substituted heterocyclic ring, and wherein each occurrence of R₉ is independently selected from the group consisting of hydrogen, halogen, optionally substituted $C_{1-10}$ alkyl, optionally substituted alkenyl, optionally substituted alkynyl, optionally substituted carbocyclyl, optionally substituted heterocyclyl, optionally substituted aryl, and optionally substituted heteroaryl, or R₉ is joined with the adjacent carbon or nitrogen or oxygen atom to form an optionally substituted carbocyclic or heterocyclic ring, or two R₉ groups are joined to form an optionally substituted carbocyclic or optionally substituted heterocyclic ring;

L₂ is a moiety derived from a crosslinking reagent capable of crosslinking the carrier and Li;
R₇ is independently hydrogen, optionally substituted $C_{1-6}$ alkyl, optionally substituted acyl, or a nitrogen protecting group.
with a proviso that when m is 1 to 2, then n is not 1 to 5.

In preferred embodiment, Li is of formula.

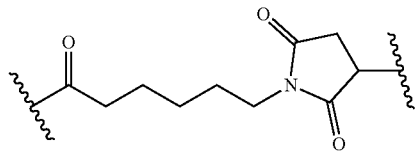 [SMILES: *C(=O)CCCCCN1C(=O)CC(*)C1=O]

In preferred embodiment, L₂ is of formula.

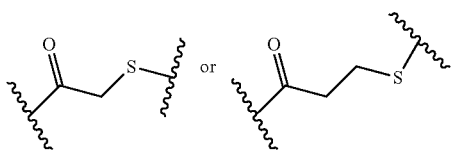 [SMILES: *SCC(*)=O ; *SCCC(*)=O]

In a preferred embodiment, the present invention relates to a synthetic meningococcal C oligosaccharide of formula (IA).

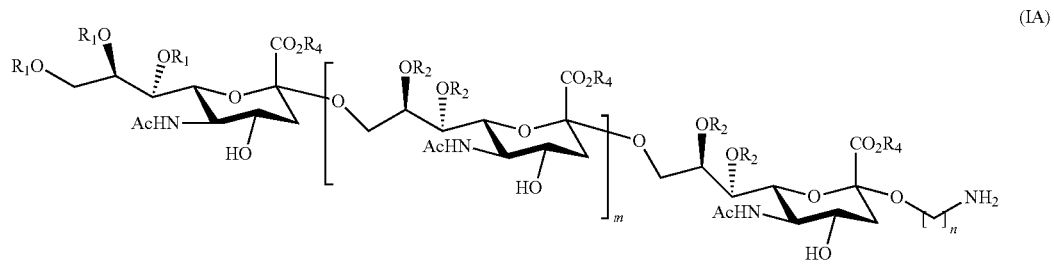
(IA)

wherein m and n are integers ranging from 1 to 10;

$R_1$ and $R_2$ are same or different and independently represent H, $C_{1-6}$alkyl, acetyl;

$R^4$ represents H, $C_{1-6}$ alkyl, alkali metal cation selected from Li, Na, K and Cs; with a proviso that when m is 1 to 2 n is not 1 to 5.

In an embodiment, the present invention also provides a process for the preparation of novel semi-synthetic meningococcal conjugate vaccine comprising the steps of:

a) synthesising meningococcal oligosaccharide of formula (I), b) activation of oligosaccharide, c) derivatization of carrier protein, d) conjugation of meningococcal oligosaccharide obtained in step (b) with carrier protein and e) purification of conjugate vaccine obtained in step (d).

In a preferred embodiment, the synthetic oligomer (sMenC) is activated using 6-maleimidohexonoic acid N-hydroxysuccinimide ester. The carrier protein is derivatized using 3-(acetyl thio) propionic acid N-hydroxysuccinimide ester.

Crosslinking reagents suited to the invention are widely known in the art (see, for example, 1994 Pierce Technical Handbook: cross-linking available at http://www.piercenet.com/resources/browse.cfm?fldlD=184).

In preferred embodiment the crosslinking reagent used to derivatize the carrier protein is

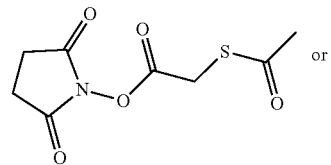 or

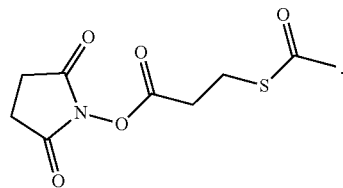

In certain embodiments, the invention provides a method of preparing a conjugate vaccine of formula (II) described herein, comprising coupling a compound of formula

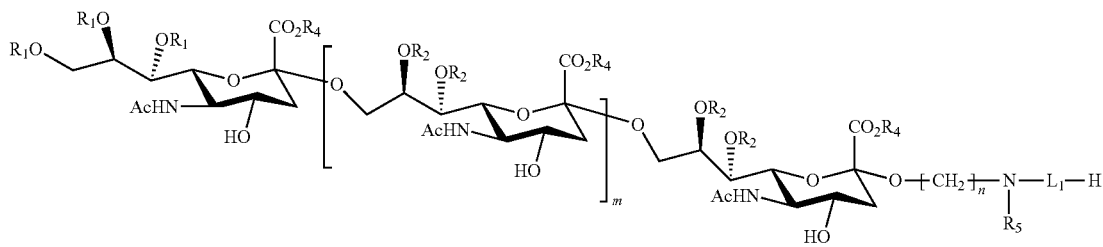

with a compound of the formula

wherein $L_2$ is a crosslinking reagent capable of crosslinking an amino group and —SH.

In another embodiment, the preferred semi-synthetic conjugate vaccine is of the formula as given below:

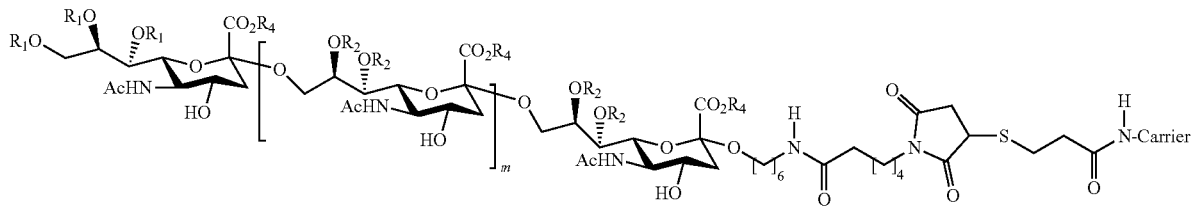

In another embodiment, the carrier is a protein, a lipid, a lipolized protein, a virus, a peptide comprising a T cell epitope, or a dendrimer of glycopeptides. In certain embodiments, the carrier is a toxin protein selected from the group consisting of diphtheria toxin cross-reacting material 197 (DT-CRM197), diphtheria toxoid (DT), tetanus toxoid (TT), and outer-membrane protein (OMP). Preferably, the carrier protein is Tetanus toxoid, diphtheria toxoid or CRM197.

The activation of oligosaccharide is carried out using bromoacetic N-hydroxysuccinimide (NHS) ester, 6-Maleimidohexanoic acid NHS ester, 6-(iodoacetamido)caproic acid NHS ester, maleimidopropionoic acid NHS ester, maleimidoacetic acid NHS ester, maleimidobenzoic acid NHS ester and the like.

The derivatization of carrier protein is carried out using 3-(acetyl thio) propionic acid N-hydroxysuccinimide ester, acetylthio-hexadecanoic acid NHS ester and the like.

The polysaccharide component manufactured using chemical process is referred to as synthetic oligosaccharide or oligomer. The conjugate construct using the synthetic oligosaccharide and a carrier protein is referred to as semi-synthetic conjugate.

As used herein the term "Men C" is referred to *Neisseria meningitidis* serogroup C component of the vaccine. The Men C Capsular polysaccharide component manufactured using chemical process is hereby referred to as sMenC Oligomer (or sMenC). sMenC is further conjugated to a carrier protein to give a semi-synthetic immunogenic composition.

As used herein the term "Oligomer" or "capsular saccharide" is referred to Oligosaccharides. The terms can be used interchangeably.

Examples of protecting groups and details of their usage are available in, for example, Greene, T. W., and Wuts, R G. M., *Protective Groups in Organic Synthesis*, 2d ed. (1991).

Following compounds are the preferred novel synthetic meningococcal oligomers of the present invention:

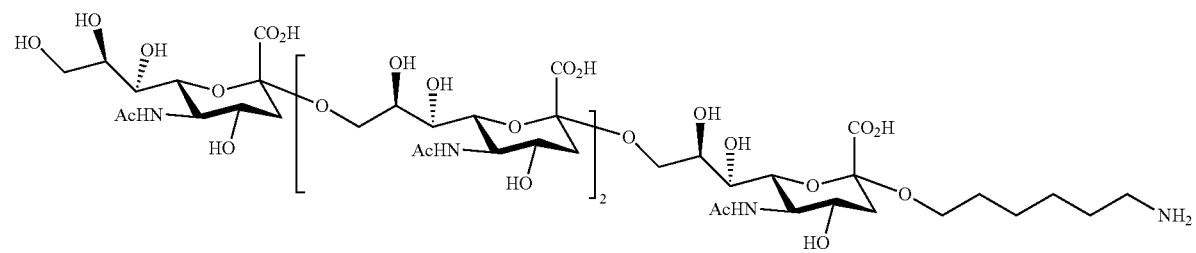

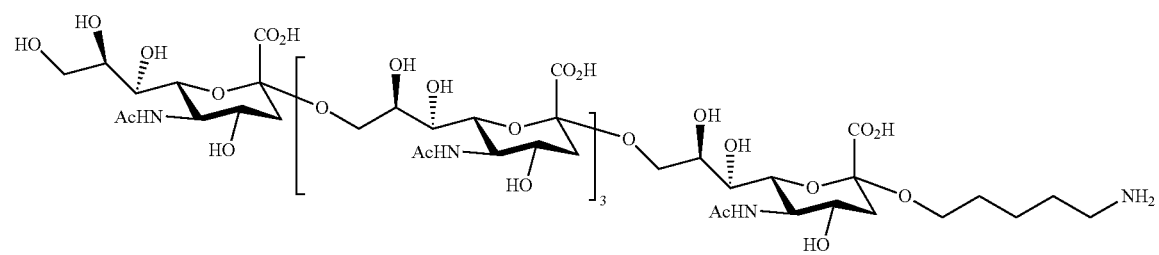

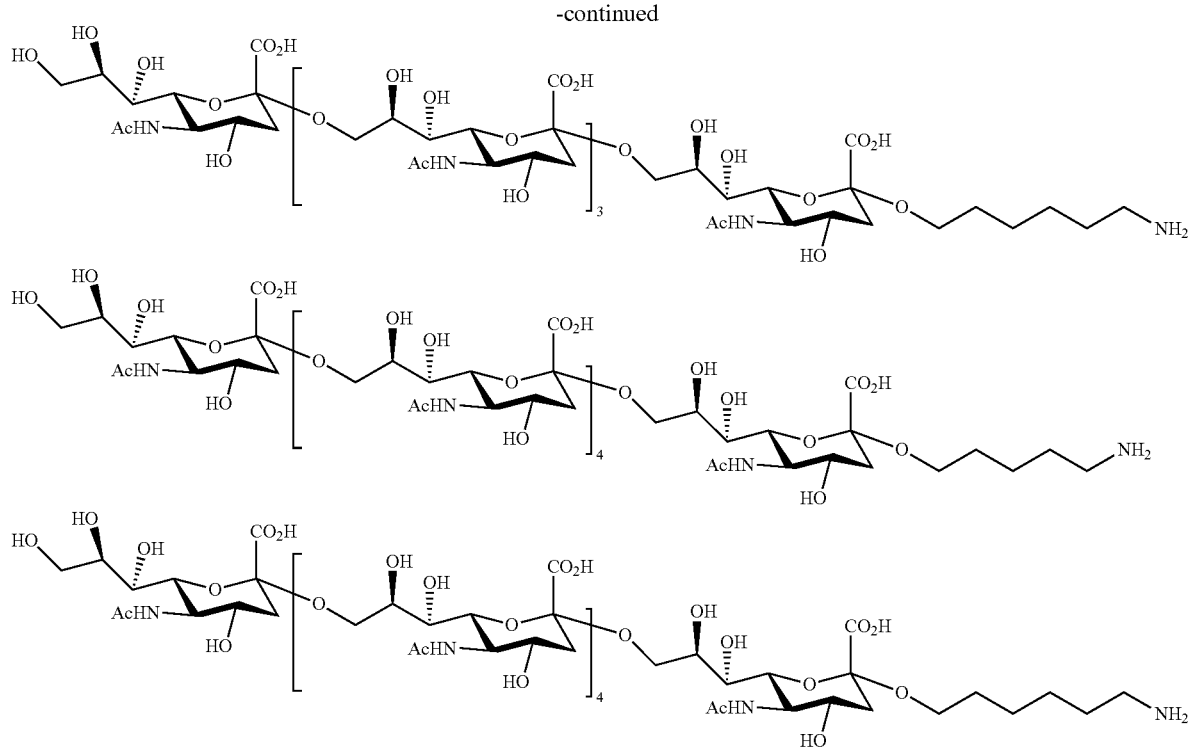
Given below are the preferred novel semi-synthetic meningococcal C conjugate vaccines of the present invention:
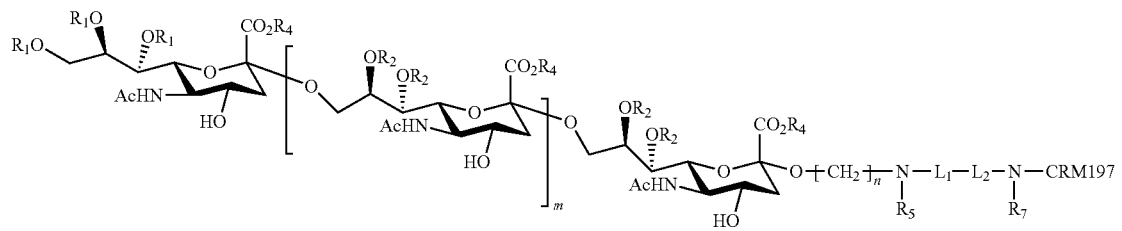
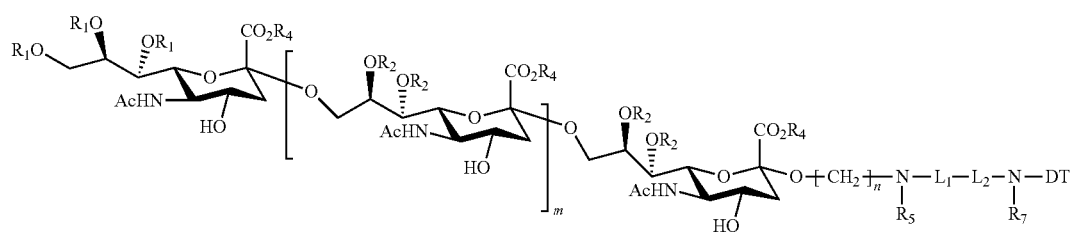
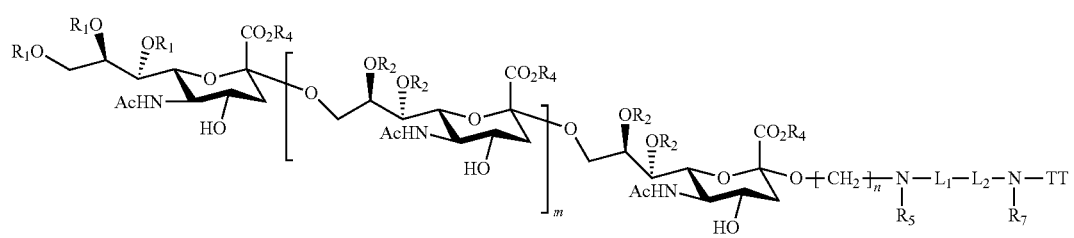

In yet another embodiment, the present invention provides a process for the preparation of sMenC Oligomer of formula (I) as shown in the scheme I given as follows:

N-Iodosuccinimide (NIS), N-Bromosuccinimide (NBS) and the like. The reaction may be carried out in the presence of catalysts such as TMSOTf, TESOTf, TfOH, Tf$_2$O, AgOTf,

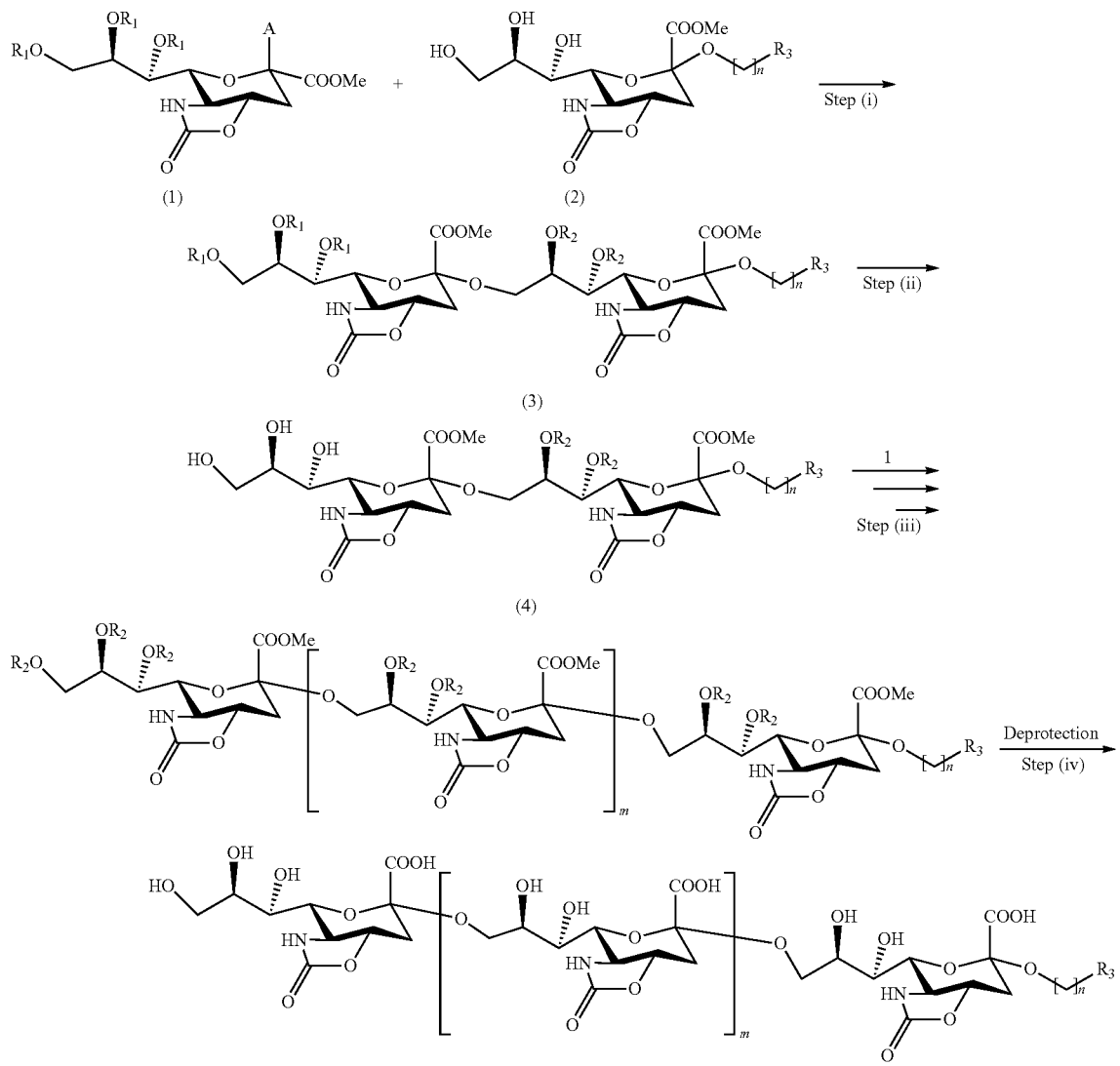

where A represents leaving group such as halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, -OTs), methanesulfonate (mesylate, -OMs), p-bromobenzenesulfonyloxy (brosylate, -OBs), or trifluoromethanesulfonate (triflate, -OTf);

R$_1$ is chloroacetate, dichloroacetate, trichloroacetate, trifluoroacetate.

Step (i):

The coupling of compound (1) and (2), followed by acetylation to yield compound of formula (3). The coupling is carried out in the presence of solvents such as dichloromethane, acetonitrile, propionitrile, ether, acetone, chloroacetonitrile, N,N-dimethylformamide, tetrahydrofuran, dimethylsulfoxide and the like or a mixture thereof using BF$_3$.Et$_2$O, lanthanide triflates and the like, at a temperature in the range of −78° C. to 25° C. for a period in the range of 1-12 hours.

Acetylation of the hydroxyl groups of the coupled product is carried out using acetic anhydride, acetyl chloride in the presence of a base such as DIPEA, TEA, imidazole, lutidine, pyridine and the like as well as TfOH, TMSOTf, BF$_3$.Et$_2$O, lanthanide triflates and the like.

Step (ii):

Dechloroacetylation is carried out in the presence of solvents such as methanol, ethanol, isopropanol, acetone, acetonitrile and the like using bases such as DIPEA, TEA, imidazole, pyridine and the like.

Step (iii):

Repetition of the sialylation, acetylation, and dechloroacetylation reactions to produce high order sialosides. This three-step sequence provides the tri- and tetrasialic acids.

Step (iv):

Deprotection and deesterification: The reaction is carried out using solvents such as ethanol, methanol, propanol, i-propanol, water and the like; and bases such as lithium hydroxide, sodium hydroxide, potassium hydroxide and the like. The reaction is carried out at a temperature in the range of 25° C. to 80° C. The resulting amines were N-acetylated using acetylating agents such as acetic anhydride, acetyl-chloride and the like in the presence of bases such as sodium hydroxide, potassium hydroxide, $NaHCO_3$, DIPEA, TEA, imidazole, pyridine and the like.

In yet another embodiment, the compound of formula (I) wherein $R_3$ represents azide is converted to amino. The reaction is carried out using reducing agents such as Pd/C, Pt/C, $LiAlH_4$, sodium borohydride and the like in a conventional method.

In an embodiment, the present invention also provides a process for the preparation of novel semi-synthetic conjugate vaccine of formula (II), which comprises the steps of:

Step 1: Derivatization of Carrier Protein.

To carrier protein 3-(Acetyl thio) propionic acid N-succinimidyl ester is added and incubated. This mixture is desalted and buffer exchanged with Phosphate-buffered saline (PBS). Further, the solution is treated with hydroxylamine hydrochloride and incubated. This mixture is desalted and concentrated.

Step 2: Activation of Oligosaccharide.

The oligosaccharide with linker is activated with 6-maleimidohexonoic acid N-hydroxysuccinimide ester and then incubated for the reaction to occur. This mixture is further desalted and concentrated.

Step 3: Conjugation:

Derivatized carrier protein and activated synthetic oligosaccharide are mixed and incubated to form the conjugate vaccine. The conjugate is purified by using diafiltration to generate bulk conjugate.

Physico-chemical aspects as well as the immunological response of the novel semi-synthetic construct is characterized by analytical methods.

The novel semi-synthetic conjugate vaccine of the present invention is physically and chemically characterized to confirm and quantify the presence of synthetic oligosaccharide. The construct is also characterized using 2D Total Correlated Spectroscopy (TOCSY) to confirm the presence of sialic acid in the semi-synthetic Meningococcal C conjugate bulk.

Physico-chemical aspects of the semi-synthetic conjugate vaccine is measured by the following techniques:
a. NMR spectra of the synthetic oligosaccharide (FIG. 1);
b. High Resolution Mass Spectroscopy (HRMS) of the synthetic Meningococcal C oligosaccharide. The HRMS confirms the molecular weight of the glycan construct. (FIG. 2);
c. TOCSY (120 ms) of semi-synthetic Meningococcal C bulk conjugate. (FIG. 3);
d. Quantification of Sialic acid in semi-synthetic Meningococcal-C Conjugate using sialic acid as reference standard by HPAEC-PAD Method (FIG. 4).

The immunogenic activity of oligosaccharides described herein is often enhanced by conjugation to a protein. Thus the invention includes conjugating the oligosaccharide to a protein through a linker moiety, which may be $L_1$ and $L_2$ in formula (II).

The immunological response was measured in mice after each dose in a 3-dose regime of semi-synthetic Meningococcal C conjugate, as compared to references such as non conjugated Quadri Meningo and conjugated Menectra®.

Mouse immunogenicity by ELISA was also done. The antibody response was measured by indirect ELISA using commercial polysaccharide coating antigen in the NUNC covalink plates. Readings were measured by using 96 well plate reader.

Identification of antigenicity by Immunodiffusion assay was also done. The antigenicity of conjugate was evaluated by use of a Meningococcal group C antisera by immunodiffusion as compared with negative purified polysaccharide of *N. meningitidis* C, which served as Positive Reference. A clear zone of antigen Vs antibody precipitate was observed.

The immunogenic compositions of the invention are suitable for use in adult humans as well as in children. Optionally, such a composition may be administered in combination with other pharmaceutically active substances, and frequently it will be administered in combination with other vaccines as part of a childhood vaccination program. Compositions for administration may beneficially include other types of immunogenic compounds such as glycoconjugates that elicit an immune response against other meningitis pathogens.

In yet another embodiment, the present invention also provides pharmaceutical compositions comprising novel semi-synthetic meningococcal C conjugate vaccine of the invention admixed with at least one pharmaceutically acceptable excipient.

The novel semi-synthetic conjugate of the present invention is demonstrated to be immunogenic in an established animal model (mice). Sera isolated after primary vaccination is demonstrated to contain antibodies specific to Meningococcal C polysaccharide (ELISA). In addition, immunodiffusion assays shows a clear precipitation band corresponding to neutralizing antibodies against meningococcal C polysaccharide.

The advantages of semi-synthetic Meningococcal conjugate vaccine, of the present invention includes:
1. The polysaccharide component is synthetically manufactured instead of being derived from a biological process. Linker with multiple carbon in the synthetic oligosaccharide construct is attached to the oligomer without the involvement of a separate process step;
2. the process of conjugation using thiol chemistry with synthetic oligosaccharide construct resulting in high yields.
3. the construction of a T-cell independent antigen (oligomer or glycan) which is transformed into a t-cell dependent antigen upon conjugation;
4. the oligosaccharides are small and has potential to conjugate with different carrier proteins.

The invention also provides vaccines and immunogenic compositions comprising synthetic capsular saccharide from *N. meningitidis* serogroup C and capsular saccharides from at least two of serogroups A, W135 and Y of *N. meningitidis*, wherein said capsular saccharides are conjugated to carrier protein(s) methods of which are known in the art. For example the following reference provide the conjugation of polysaccharides to carrier protein.
1. Joanna Kubler-Kielb and Vince Pozsgay, National Institute of Child Health and Human Development, National Institutes of Health, 31 Center Dr. MSC 2423 Bethesda, Md.;
2. Joanna Kubler-Kielb et al., Oligosaccharide conjugates of *Bordetella pertussis* and *bronchiseptica* induce bactericidal antibodies, an addition to pertussis vaccine, PNAS 2011, 108:4087-92;
3. Joanna Kubler-Kielb and Vince Pozsgay, A New Method for Conjugation of Carbohydrates to Proteins Using an Aminooxy-Thiol Heterobifunctional Linker, J. Org. Chem. 2005, 70, 6987-6990;

4. J. Kubler-Kielb, E. Vinogradov, G. Ben-Menachem, V. Pozsgay, J. B. Robbins, R. Schneerson, Saccharide/protein conjugate vaccines for *Bordetella* species: preparation of saccharide, development of new conjugation procedures, and physico-chemical and immunological characterization of the conjugates. Vaccine 2008, 26: 3587-93.

The present invention provides a kit comprising: (a) synthetic capsular saccharide from *N. meningitidis* serogroup C; conjugated to a carrier protein (b) capsular saccharides from *N. meningitidis* serogroups A, W135 and Y, conjugated to a carrier protein.

In yet another embodiment, the conjugated synthetic capsular saccharide from *N. meningitidis* serogroup C has a saccharide:protein ratio (w/w) of between 0.1:1 and 2:1.

In yet another embodiment, the present invention provides an immunogenic composition comprising novel semi-synthetic conjugate vaccine containing the 1 μg to 10 μg of synthetic men C oligosaccharide conjugated to 5 to 20 μg of carrier protein. The present invention further comprises, 1 μg to 10 μg of each polysaccharide selected from Meningococcal serogroups A, Y and W-135, each conjugated individually to 5 to 20 μg of carrier protein.

The vaccines and pharmaceutical compositions of the invention are intended for parenteral, topical, oral or local administration. Preferably, they are administered parenterally, e.g., intravenously, subcutaneously, intradermally, or intramuscularly. Thus, the invention provides compositions for parenteral administration which comprise a solution of the immunogenic moiety dissolved or suspended in an acceptable excipient, preferably a primarily aqueous carrier. A variety of aqueous carriers may be used, e.g., water, buffered water, 0.8% saline, 0.3% glycine, hyaluronic acid and the like. These compositions may be sterilized by conventional sterilization techniques, or may be sterile filtered. The resulting aqueous solutions may be packaged for use as is, or lyophilized, the lyophilized preparation being combined with a sterile solution prior to administration.

The invention provides an immunogenic composition comprising semi-synthetic meningococcal C oligosaccharide conjugate, and further comprising (i) an aluminium phosphate or an aluminium hydroxide adjuvant (ii) a buffer preferably a phosphate buffer and optinally one or more excipients selected from sucrose, polysorbate and trometamol and the like The invention also provides the use of a synthetic capsular saccharide from *N. meningitidis* serogroup C, or of a conjugate thereof, in the manufacture of a medicament for preventing or treating a disease caused by capsulate bacteria. Diseases caused by *Neisseria* include meningitis, septicemia and gonorrhea. Diseases caused by *H. influenzae* include otitis media, bronchitis, pneumonia, cellulitis, pericarditis, and meningitis. Diseases caused by *Pneumococcus* include meningitis, sepsis and pneumonia.

The following examples are provided to illustrate the invention and are merely for illustrative purpose only and should not be construed to limit the scope of the invention.

Example 1

Preparation of Compound 2

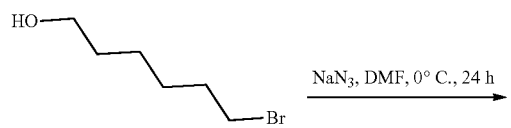

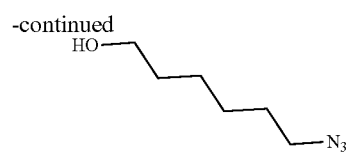

To a stirred solution of 6-bromo-1-hexanol (25 g, 0.138 mol) in DMF, sodium azide (18 g, 0.277 mol) was added at 0° C. and stirred RT for 24 h. The reaction mixture was quenched with ice-cold water and extracted with diethyl ether. Organic layer was washed with brine, separated, dried over $Na_2SO_4$ and concentrated. 6-azido-1-hexanol was obtained as colorless liquid (17 g, 75%).

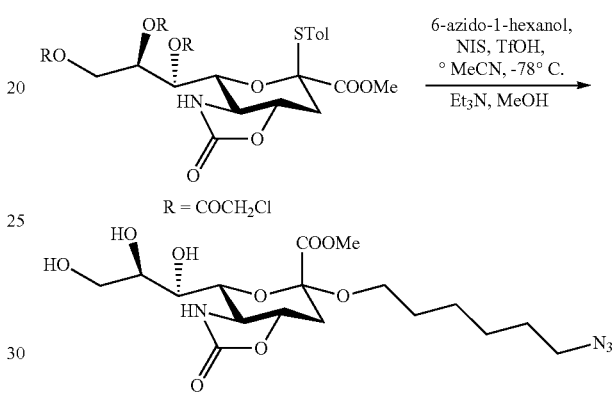

To a stirred solution of Compound-1 (40 g, 62.30 mmoles) and 6-azido-1-hexanol (10.6 g) in DCM (265 ml) and acetonitrile (135 ml) was added MS 4A° (40 g), cooled to −78° C. To this mixture NIS (20.04 g, 89.09 mmoles), TfOH (2.65 ml, 18.6 mmoles) were added. Reaction temperature was raised to −50° C. and stirred for 30 mins. The reaction mixture was quenched with saturated hypo solution (150 ml), filtered through celite, organic layer was separated, washed with water, dried $Na_2SO_4$ and concentrated. Crude compound was purified by FCC by eluting with 10-20% ethyl acetate and hexanes, compound-1a was obtained as an off-white sticky solid (28 g, 65%).

To a stirred solution of compound-1a (34 g, 51.5 mmol) in methanol (1.3 lit), triethyl amine (7.1 ml, 51.5 mmol) was added to the reaction mixture at 0° C. and stirred for 30 minutes at RT. After completion, the reaction mixture was neutralized (pH 7) with 10% HCl solution and reaction mixture was concentrated under reduced pressure. Crude compound was purified by FCC, by eluting with (1:1:0.1) ethyl acetate, hexanes and methanol. Compound 2 was obtained as sticky solid (14 g, 60%).

Preparation of Compound 3

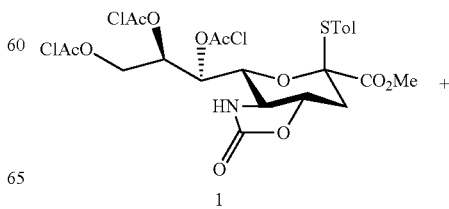

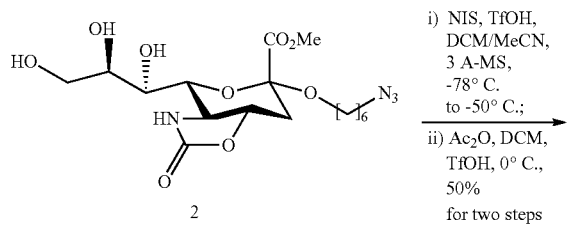

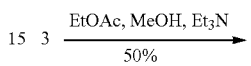

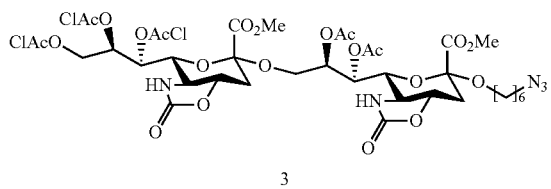

(i) To a stirred mixture of Compound 1 (40 g, 62.30 mmoles, prepared as described in *J. Org. Chem.*, 2010, 75, 4921-4928) and Compound 2 (10.65 g) in DCM (140 ml) and acetonitrile (70 ml) was added MS 3A° (20 g), cooled to −78° C. To this mixture NIS (6.937 g, 44.102 mmoles), Triflic acid (1.28 ml, 14.494 mmoles) were added. Reaction temperature was raised to −50° C. and stirred for 30 mins. The reaction mixture was quenched with saturated $Na_2S_2O_3$ solution (150 ml), filtered through celite, organic layer was separated, washed with water, dried $Na_2SO_4$ and concentrated. Crude compound (31 g) was put into next step.

(ii) To the solution of the crude material in $CH_2Cl_2$ (400 ml), cooled to 0° C., $Ac_2O$ (11.65 ml, 123.364 mmoles) and TfOH (0.272 ml, 3.084 mmoles) were added. Reaction was stirred at 0° C. for 15 min and then quenched with saturated $NaHCO_3$ solution. The organic layer was separated, washed with brine solution, dried over $Na_2SO_4$ and concentrated. The dimer 3 (17 g, 50% for 2 steps) was isolated by FCC eluting with 50-60% ethyl acetate; hexanes as an off-white solid.

Preparation of Compound 4

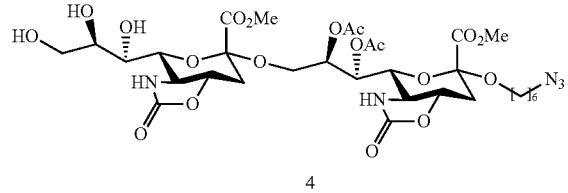

To a stirred solution of dimer 3 (16 g, 15.46 mmol) in MeOH (600 ml) and EtOAc (100 ml), $Et_3N$ (2.15 ml, 15.46 mmoles) was added to the reaction mixture at 0° C. and stirred for 30 minutes at room temperature.

Then the reaction mixture was neutralized to pH 7 with 10% HCl solution and concentrated. The product 4 was isolated by FCC eluting with (1:1:0.1) ethyl acetate, hexanes and methanol as white solid (6 g, 50%).

Preparation of Compound 5

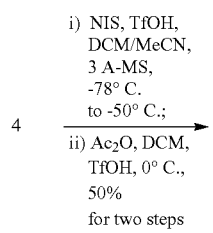

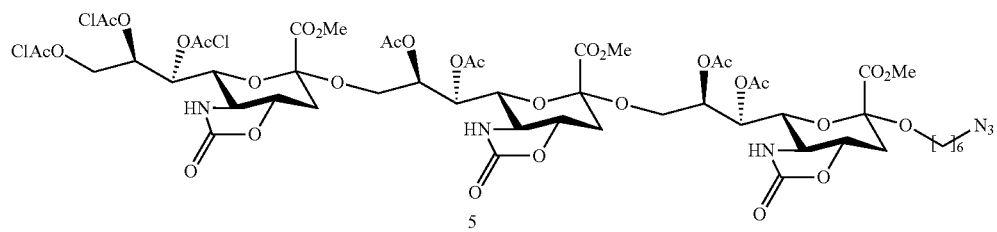

Compound 1 (5 g, 7.453 mmoles) and compound 4 (5 g, 6.211 mmoles) were coupled using similar method described for dimer 3 step i (DCM 40 ml, $CH_3CN$ 20 ml, MS 3A° 3.1 g, NIS 2.5 g, TfOH 0.275 ml). The Crude compound (10 g) was put into next step without purification.

The crude product was treated in a similar method as described for dimer 3 step ii (DCM 100 ml, $Ac_2O$ 2.95 ml, TfOH 0.137 ml). The trimer 5 (4.3 g, 40% for 2 steps) was isolated by FCC eluting with 50-60% ethyl acetate; hexanes as an off-white solid.

Preparation of Compound 6

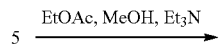

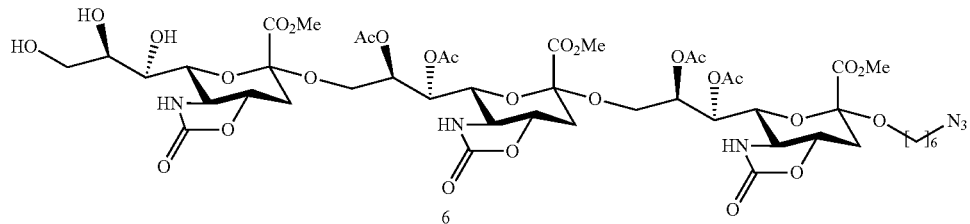

Trimer 5 (4.8 g, 3.409 mmol) was treated in a similar method as described for compound 4 (MeOH 190 ml, EtOAc 37 ml, $Et_3N$ 0.473 ml, 3.409 mmoles). The product 6 (2 g, 45%) was isolated by FCC eluting with (1:1:0.2) ethyl acetate, hexanes and methanol as white solid.

Preparation of Compound 7

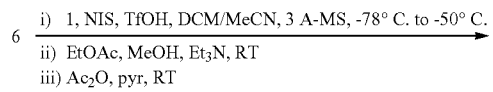

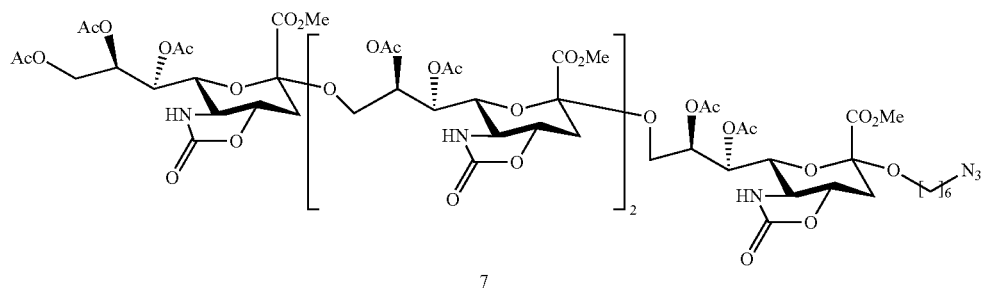

(i) Compound 1 (1.308 g, 2.307 mmoles) and Compound 6 (2 g, 1.697 mmoles) were coupled using similar method described for dimer 3 step i (DCM 16 ml, $CH_3CN$ 8 ml, MS 3A° 0.85 g, NIS 0.687 g, TfOH 0.072 ml). Crude compound (3 g) was put to next step without purification.

(ii) The crude compound was treated in a similar method as described for compound 4 (MeOH 100 ml, EtOAc 15 ml, $Et_3N$ 0.25 ml). Crude compound (3 g) was put to next step without purification.

(iii) To a stirred solution of above crude product in pyridine (4 ml), acetic anhydride (2 ml) was added and stirred at RT for 24 h. Tetrasialoside 7 (1 g, 35%) was isolated by FCC eluting with (1:1:0.2) ethyl acetate, hexanes and methanol as white solid.

Preparation of Compound 8

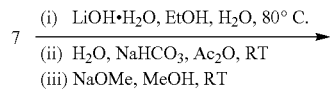

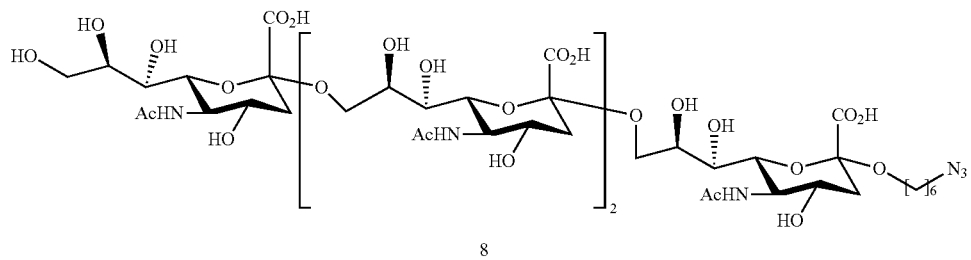

(i) To a stirred solution of tetrasialoside 7 (1 g, 0.5963 mmoles) in ethanol (60 ml) and water (60 ml) was added lithium hydroxide monohydrate (0.75 g, 17.889 mmoles) and reaction was maintained at 80° C. for 24 h. Reaction mixture was neutralized with 10% HCl solution and then was concentrated.

(ii) The residue (1.8 g) was dissolved in water (20 ml), and then NaHCO$_3$ (1 g, 11.926 mmoles) followed by acetic anhydride (0.608 g, 5.963 mmoles) were added at RT. After being stirred for additional 16 h, the solvent was evaporated under reduced pressure and the crude was put into next step (iii) The residue was dissolved in methanol (20 ml) and then NaOMe (0.65 g, 11.926 mmoles) was added at RT. After being stirred for 16 h, the reaction mixture was neutralized with Dowex WxB 50*8 resin and the neutralized solution filtered and was concentrated. The residue was purified by P2 Biogel, eluting with water. Obtained product was lyophilized to give tetrasialic acid 8 as white solid (0.5 g, 60% for 3 steps).

Preparation of Tetramer of Compound 9

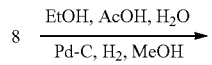

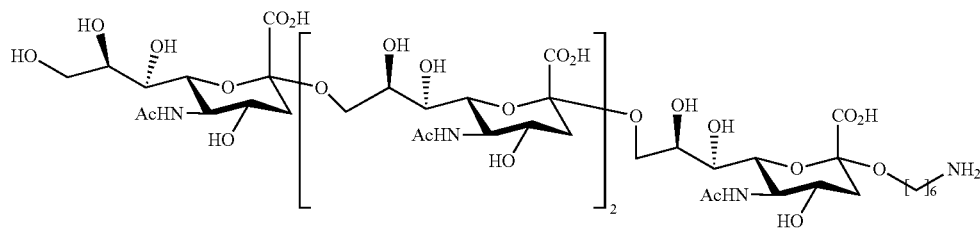

To a stirred solution of tetrasialic acid 8 (0.5 g, 0.3825 mmoles) in ethanol (20 ml) and water (10 ml), were added acetic acid (10 ml) and 10% Pd/C (0.2 g). After purging with N$_2$, the reaction mixture was filtered through celite and concentrated under reduced pressure at RT. Product was purified by Sephadex-G-10, eluting with water. Obtained product 9 was lyophilized to get the required product as white solid (0.3 g, 60%).

Example 2

Derivatization of Carrier Protein for Conjugation

Tetanus toxoid was concentrated and buffer exchanged with 10 mM PBS to 5 to 20 mg/ml. To this 25 molar equivalent of 3-(acetyl thio) propionic acid N-hydroxysuccinimidyl ester was added against the amine molar concentration. After which it was finally incubated at room temperature for 2 hours.

After the incubation period, the reaction mixture was desalted and buffer exchanged with 10 mM PBS using a 10 kD cut-off membrane filter. It was deacetylated using hydroxylamine hydrochloride and then incubated at room temperature for 2 hours. Finally it was desalted and concentrated with 10 mM PBS.

Example 3

Activation of Oligosaccharide

Firstly the amine concentration of oligomer was estimated by TNBS assay. Then 1.5 molar equivalent of 6-maleimidohexonoic acid N-hydroxysuccinimide ester was added respective to oligomer amine molar concentration. This reaction mixture was incubated at room temperature for 5 hours. After this, the derivatized oligomer was dried using vacuum for one hour. It was then desalted and buffer exchanged with 10 mM PBS using chromatography and concentrated to about 5 to 10 mg/ml.

Example 4

Conjugation of Synthetic Oligosaccharide with Carrier Protein

The synthetically prepared oligomer was conjugated with carrier protein (TT) using thiol chemistry, where both the activated oligomer and derivatized TT prepared as above were mixed and incubated at 2 to 8° C. for 96 hours.

After the conjugate was formed, it was purified and followed by buffer exchange with 1×PBS for which 10 kD cut-off membrane filter was used. Finally it was filtered through 0.2µ filter.

Example 5

Test for Immunogenicity of Semi-Synthetic Oligosaccharide Vaccine

Mouse immunogenicity study of the semi-synthetic meningococcal serogroup C conjugate formulation was done. It was administered through subcutaneous route. A group of 10 mice were immunised with 3 doses of vaccine and each time the terminal bleed was taken after 7 days. Control group receiving Menactra received 2 doses. Following this, anti-meningococcal C (Men-c) polysaccharide IgG antibody levels were measured by a serotype specific ELISA. Similarly sera from terminal bleeds of 10 mice immunized with Menactra were pooled and used. Antibody concentration for standard was assigned with arbitrary value of 100 units/ml. Antibody concentration for test vaccine formulation were calculated in relation to the standard.

Geometric mean antibody concentration following First dose of semi-synthetic Men C was found to be 1.4, a significant increase was observed following the Second dose to give a mean antibody concentration of 176.23 units/ml. This was analogous with a memory response and all mice showed increased antibody content. Mean antibody concentration increased following the Third dose to 412.5 units/ml. (FIG. 5 and FIG. 6). This indicates that semi-synthetic formulation elicited an antibody response with a similar profile to a classical conjugate vaccine.

To determine functional antibodies in response to vaccination Serum Bactericidal Assay (SBA) was performed. The sera was acquired following immunization with semi-synthetic Men C conjugate composition, Control Sera was obtained from mice immunised with Quadri Meningo and Menactra®. Analysis of variance between all the groups showed a significant difference (p=0.00). Interrogation of the difference between the groups, performed using Dunnerr test with multiple comparisons, demonstrated significantly higher titres for the CONTROL groups i.e. Quadri Meningo Vaccine sera (p-0.00) and Menactra® vaccine sera (p=0.003) (FIG. 7).

Hence, high concentration of functional IgG antibodies capable of killing *Neisseria meningitidis* in the SBA was found for sMen-C preparation given at a 2.5 µg immunisation dosage.

The invention claimed is:

1. A semisynthetic meningococcal C conjugate vaccine, comprising: a synthetic meningococcal C oligosaccharide, wherein the synthetic meningococcal C oligosaccharide is conjugated to a carrier protein to form the semisynthetic meningococcal C conjugate vaccine having Formula (II):

(II)

[Structure of Formula (II)]

wherein m is an integer 2 and n is an integer 6;
$R_1$, $R_2$, and $R_4$ are each H;
$R_5$ is H;
CP represents a carrier protein;
$L_1$ is

[Structure]

;

$L_2$ is a moiety derived from a crosslinking reagent capable of crosslinking the carrier protein and $L_1$, wherein $L_2$ is selected from

[Structure] or [Structure] ;

and
$R_7$ is H.

2. The semisynthetic meningococcal C conjugate vaccine of claim 1, wherein the carrier protein is selected from the group consisting of tetanus toxoid, diphtheria toxoid, and $CRM_{197}$.

3. A pharmaceutical composition comprising (a) the semisynthetic meningococcal C conjugate vaccine of claim 1 and (b) a pharmaceutically acceptable carrier.

4. The pharmaceutical composition of claim 3, further comprising a polysaccharide selected from the group consisting of serogroups A, W135, and Y of *Neisseria meningitidis*, wherein the polysaccharide is conjugated to a carrier protein.

5. The pharmaceutical composition of claim 4, further comprising a vaccine adjuvant.

6. The pharmaceutical composition of claim 5, wherein the pharmaceutical composition protects against a disease caused by *Neisseria meningitidis*.

7. The pharmaceutical composition of claim 3 further comprising a polysaccharide of Meningococcal serogroup A, Meningococcal serogroup Y, and Meningococcal serogroup W135, wherein the composition comprises about 1 µg to about 10 µg of Meningococcal serogroup A, about 1 µg to about 10 µg of Meningococcal serogroup Y, and about 1 µg to about 10 µg of Meningococcal serogroup W135, and wherein each of polysaccharide is individually conjugated to about 5 to about 20 µg of a carrier protein.

* * * * *